United States Patent [19]

Kelman

[11] Patent Number: 4,477,931
[45] Date of Patent: Oct. 23, 1984

[54] INTRAOCULAR LENS WITH FLEXIBLE C-SHAPED SUPPORTS

[76] Inventor: Charles D. Kelman, 269 Grand Central Pkwy., Floral Park, N.Y. 11005

[21] Appl. No.: 477,020

[22] Filed: Mar. 21, 1983

[51] Int. Cl.³ .......................... A61F 1/16; A61F 1/24
[52] U.S. Cl. .......................................................... 3/13
[58] Field of Search .......................................... 3/13, 1

[56] References Cited

U.S. PATENT DOCUMENTS

| | | | |
|---|---|---|---|
| 4,110,848 | 9/1978 | Jensen | 3/13 |
| 4,280,232 | 7/1981 | Hummel | 3/13 |
| 4,328,595 | 5/1982 | Sheets | 3/13 |
| 4,343,050 | 8/1982 | Kelman | 3/13 |
| 4,363,143 | 12/1982 | Callahan | 3/13 |

FOREIGN PATENT DOCUMENTS 563174  7/1977  U.S.S.R. ................................... 3/13

Primary Examiner—Ronald L. Frinks
Attorney, Agent, or Firm—Henry Sternberg

[57] ABSTRACT

An intraocular posterior chamber lens which has two resilient support portions with protruding contact points for seating the lens in the lower groove portion formed by the anterior and posterior capsules of the eye. The lens also includes an upwardly extending stabilizing portion adapted to be positioned posteriorly of the iris of the eye without being seated in the upper groove portion of the eye. The stabilizing portion provides vertical stabilization of the lens in the eye. The lens can be easily implanted in the posterior chamber of the eye and can be easily removed by a surgeon at a later date, if necessary, without substantial damage to the eye.

10 Claims, 5 Drawing Figures

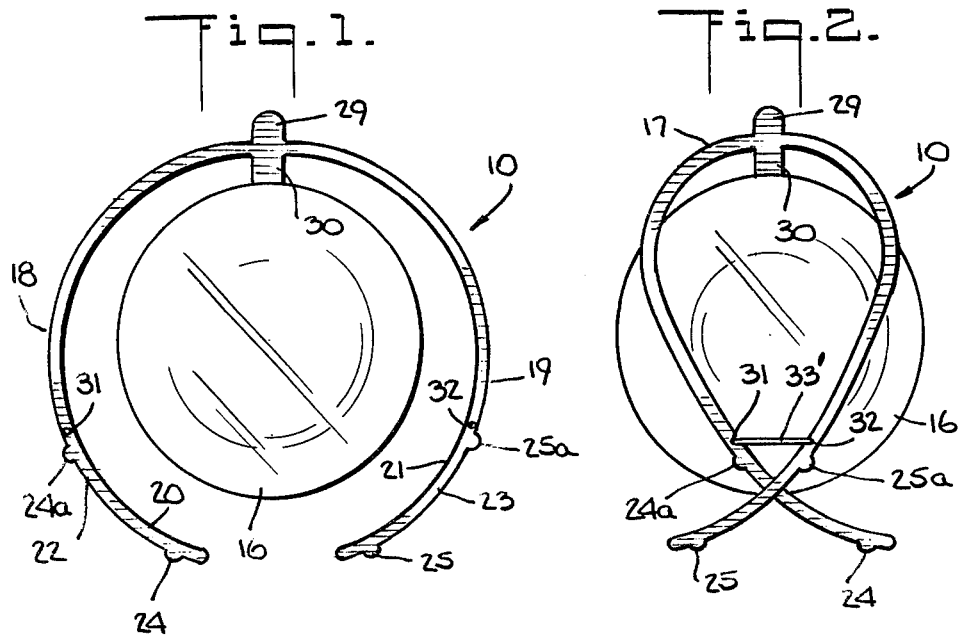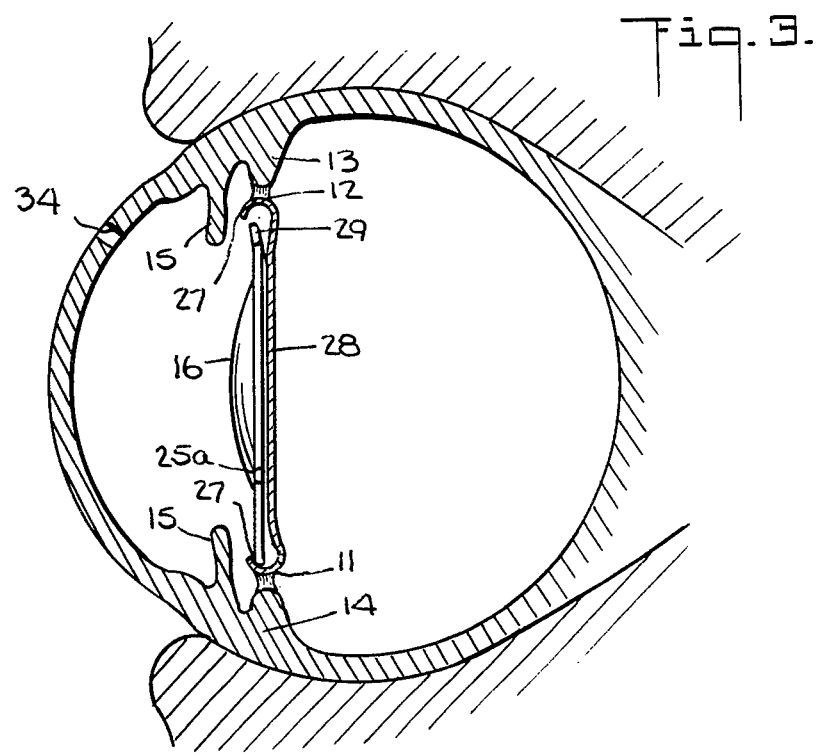

INTRAOCULAR LENS WITH FLEXIBLE C-SHAPED SUPPORTS

This invention relates to intraocular lenses and, more particularly, to intraocular lenses of the type suitable for use in the posterior chamber of the human eye after the removal of a natural lens as the result of a cataract condition.

Preparatory to removal of a cataract, the surgeon makes an opening in the anterior capsule so as to expose a portion of the natural lens. The opening is typically generally triangular in shape with substantially more of the anterior capsule remaining in the lower or inferior portion of the capsule than remains in the upper or superior portion. When seating a posterior chamber lens in the cul-de-sac formed between the anterior capsule and the posterior capsule, it is easier to seat the lens in the lower portion of the capsule where more anterior capsule tissue is present than it is to seat the lens in the upper portion where no, or only little, anterior tissue remains. It is also easier subsequently to remove the lens from the lower portion of the capsule by sliding the lens out towards the incision in the cornea of the eye than it is to remove the lens from the upper portion of the capsule since the lens has to be rocked back and forth to remove it from the upper portion of the capsule, and in so doing, the lens may tear the capsule.

Prior posterior chamber lenses, particularly since they are designed to seat in the lower, as well as in the upper portions of the capsule, have been subjected to the above-mentioned limitations. One such posterior chamber lens is disclosed and claimed in my U.S. Pat. No. 4,343,050 and is represented in FIGS. 3–6 thereof. The lens specifically disclosed in my U.S. Pat. No. 4,343,050 has two position fixation members which are generally "C"-shaped when seated in the capsule of the eye and which have notched regions, and an additional position fixation stabilizing member is also provided primarily to maintain the lens in the proper position with respect to the vertical plane of the lens body but is seated in the upper portion of the capsule.

While this lens is satisfactory, there is a need for a lens which can be easily implanted in the posterior chamber of the eye and which can be easily removed by a surgeon without substantial damage to the eye during implantation and which will facilitate removal of the lens at a later date should such removal be indicated.

In accordance with the invention, an intraocular lens with flexible support suitable for use as an artificial lens in the interior of a human eye, the eye interior having first and second groove portions extending peripherally at lower and upper portions of the eye when viewed in cross-section and having an iris disposed anteriorally of the groove portions, comprises a light-focusing lens body and position fixation means extending from the lens body and comprising first and second support portions extending generally around substantially the entire periphery of the lens body. Each of the first and second portions are generally C-shaped with the respective inner concave edges of the support portions facing each other and the outer, generally convex, edge of each of the support portions comprising at least one protruding contact point for seating each of the respective support portions in the first groove portion of the eye. The first and second support portions are resiliently deformable, in response to a force applied thereto prior to seating of the lens in the eye, and are capable of spontaneously returning toward substantially their undeformed condition upon removal of the applied force for seating the lens in the eye. The lens also comprises a stabilizing portion extending in a direction outwardly of the lens body toward the second groove portion of the eye without being seated therein.

It is an object of the present invention, therefore, to provide a new and improved intraocular lens which avoids one or more of the above-mentioned limitations and disadvantages of prior such lenses.

It is another object of the invention to provide a new and improved posterior chamber intraocular lens which avoids one or more of the above-mentioned limitations and disadvantages of prior such lenses.

It is another object of the invention to provide a new and improved posterior chamber intraocular lens which can be easily fixed in position in the eye.

It is another object of the invention to provide a new and improved posterior chamber intraocular lens which is easily removable from the eye.

It is another object of the invention to provide a new and improved posterior chamber intraocular lens which is easily removable from the superior portion of the eye.

For a better understanding of the present invention, together with other and further objects thereof, reference is made to the following description taken in connection with the accompanying drawings, and its scope will be pointed out in the appended claims.

FIG. 1 is a plan view of an embodiment of the present invention in an undeformed condition;

FIG. 2 is a plan view of the intraocular lens structure of FIG. 1 as deformed for insertion and position fixation within an eye;

FIG. 3 is a partly diagrammatic view, in section, of an eye with the FIG. 1 intraocular lens positioned therein;

Figure 4:
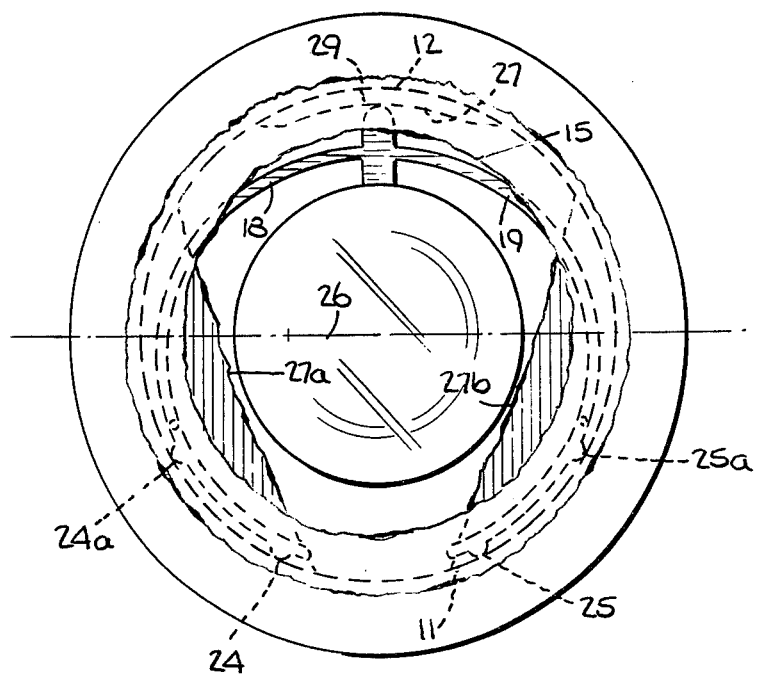
FIG. 4 is a fragmentary, diagrammatic plan view of an eye having the FIG. 1 lens positioned therein and corresponding to the sectional view of FIG. 3.

Referring now more particularly to FIGS. 1, 3 and 4 of the drawings, an intraocular lens 10 with flexible support suitable for use as an artifical lens in the interior of a human eye is represented in undeformed condition in FIG. 1. The interior of the eye, represented diagrammatically in section in FIG. 3 and in fragmentary, plan view in FIG. 4, has first and second groove portions 11, 12 at lower and upper portions 14, 13 of the eye when viewed in cross-section and has an iris 15 disposed anteriorly of the groove portions 11, 12. As best seen in FIG. 4, the anterior capsule 27 has a generally triangular opening leaving portions 27a and 27b thereof forming pockets with the posterior capsule in the lower portion of the capsule, said pockets extending substantially along said first groove portion and beyond the equator 26.

The lens 10 comprises a light-focusing lens body 16 and includes position fixation means 17 extending from the lens body 16 and comprising first and second support portions 18, 19 extending generally peripherally of the lens body 16. The lens body 16 may be constructed of any biologically inert and transparent material suitable for optical correction such as polymethylmethacrylate, quartz, opthalmic glass, and other materials known in the art. Each of the first and second support portions 18, 19 is generally "C" shaped with the respective inner concave edges 20, 21 of the support portions 18, 19 facing each other and with the outer convex edge 22, 23 of each of the support portions 18, 19 comprising at least one protruding contact point 24, 24a, 25, 25a for seating each of the respective support portions 18, 19 in the first groove portion 11 of the eye. The first and second support portions 18, 19 of the position fixation means 17 extend generally around substantially the entire periphery of the lens body 16. As represented in FIG. 4, the eye interior has an equator 26, represented in broken-line construction, at which the first and second groove portions 11, 12 meet. Both of the protruding contact points 24, 24a, 25, 25a of each of the support portions preferably are positioned for seating substantially below the equator of the eye interior. At least one of the protruding contact points of each of the support portions, namely, contact points 24, 25, is positioned near the end of the corresponding support portions 18, 19.

As represented in FIGS. 3 and 4, the first groove portion 11 of the eye interior is in the cul-de-sac formed between the anterior and posterior capsules 27, 28 in the region of the portion 27a, 27b of the anterior capsule and each support portion has at least two protruding contact points 24, 24a, 25 25a for seating each of the respective support portions 18, 19 therein. The second groove portion 12 of the eye interior is also in the cul-de-sac formed between the anterior and posterior capsules 27, 28 but in this region of the capsule substantially all of the anterior capsule is typically cut away.

The position fixation support portions 18, 19 are resiliently deformable, in response to a force supplied thereto prior to seating of the lens in the eye, and are capable of spontaneously returning toward substantially their undeformed condition upon removal of the applied force for seating the lens in the eye. The position fixation support portions 18, 19 are represented in their deformed condition in FIG. 2. As represented in FIG. 2, the position fixation support portions 18, 19 are deformable toward each other in response to the force applied thereto prior to seating of the lens in the eye.

The lens also comprises a stabilizing portion 29 extending in a direction outwardly of the lens body toward the second groove portion 12 of the eye without being seated therein. As represented in FIG. 1, the stabilizing portion 29 extends outwardly from the position fixation means 17. The position fixation means 17 has a single stem portion 30 jointed to the lens body 16, and the remaining portions of the position fixation means 17 and the stabilizing portion 29 extend from the single stem portion 30 of the position fixation means. As represented in FIG. 3, the stabilizing portion 29 extends beyond the iris 15 of the eye toward the cul-de-sac between the anterior and posterior capsules 27, 28. The position fixation means 17 and the stabilizing portion 29 may be molded integrally with the lens body 16, machined integrally with the lens body 16, or connected by welding, fusion, or any other connection method known in the art. The position fixation means 17 and the stablizing portion 29 are constructed of biologically inert and nonabsorbative material such as polymethylmethacrylate, platinum and the like.

To insert and seat the lens 10 in an eye, the surgeon may deform the support portions 18, 19 to the position represented in FIG. 2 where the maximum horizontal dimension across the lens is the diameter of the lens body 16. The support portions 18, 19 may be maintained in position by a suture 33' passing through holes 31, 32 in support portions 18, 19. The lens may then be inserted through groove portion 11 between the posterior capsule 28 and the remaining portions 27a and 27b (FIG. 4) of the anterior capsule 27. The stabilizing portion 29 may then easily be positioned by the surgeon posteriorly of the iris extending toward the groove portion 12 without being seated therein. The stabilizing portion 29 preferably is sufficiently long that it would contact the iris even when the pupil is dilated to prevent the lens from falling forward in the eye and to stabilize the lens vertically. The suture 33' may then be cut so that the support portions 18, 19 of the lens may resiliently move toward their undeformed condition and may be adjusted by the surgeon to the position represented in FIG. 4. As represented in FIG. 4, the protruding contact points 24a, 25a, 24, 25 make contact with the lower groove portion 11.

Because the stabilizing portion 29 is sufficiently short that it is not seated in the upper groove portion 12, the lens 10 can be easily implanted in the posterior chamber of the eye and can be easily removed by a surgeon at a later date, if necessary, without substantial damage to the eye.

Figure 5:
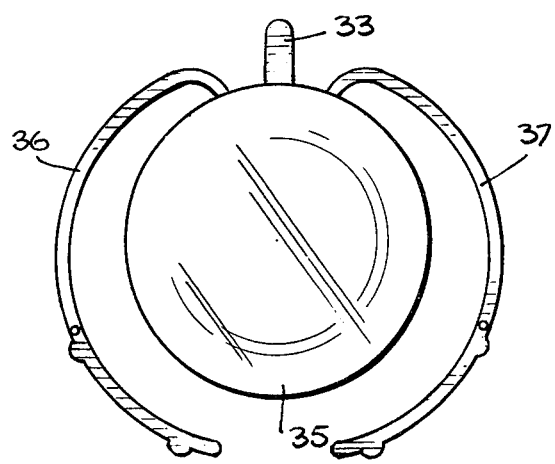
FIG. 5 is a plan view of an intraocular lens in accordance with another embodiment of the present invention.

Referring now more particularly to FIG. 5 of the drawings, there is represented an alternate embodiment of the invention in which the lens body 35 is similar to the lens body 16 of the FIG. 1 embodiment, and the support portions 36, 37 are similar to the support portions 18, 19 of the FIG. 1 embodiment except that the support portions 36, 37 individually extend from the periphery of the lens body 35. A stabilizing member 33 similar to the stabilizing portion 29 of the FIG. 1 embodiment extends from the periphery of the lens body 35 between the support portions 36, 37.

The lens of the FIG. 5 embodiment may be positioned and seated in a manner similar to that described in connection with the lens of the FIG. 1 embodiment.

While there have been described what are at present considered to be the preferred embodiments of this invention, it will be obvious to those skilled in the art that changes and modifications may be made therein without departing from the invention, and it is, therefore, aimed to cover all such changes and modifications as fall within the true spirit and scope of the invention.

What is claimed is:

1. An intraocular lens with flexible support suitable for use as an artifical lens in the interior of a human eye, said eye interior having first and second groove portions extending peripherally at lower and upper portions of the eye when viewed in cross-section and having an iris disposed anteriorly of said groove portions, said lens comprising a light-focusing lens body, position fixation means extending from said lens body and comprising first and second support portions extending generally around substantially the entire periphery of said lens body, each of said first and second support portions being generally "C" shaped with the respective inner concave edges of the support portions facing each other and the outer generally convex edge of each of the support portions comprising at least one protruding contact point for seating each of the respective support portions in said first groove portion of the eye, said first and second support portions being resiliently deformable, in response to a force applied thereto prior to seating of the lens in the eye, and being capable of spontaneously returning toward substantially their undeformed condition upon removal of said applied force for seating said lens in the eye, said lens also comprising a stabilizing portion extending in a direction outwardly of said lens body toward said second groove portion of the eye without being seated therein.

2. An intraocular lens in accordance with claim 1 in which the eye interior has an equator at which said first and second groove portions meet and each of said support portions has at least two protruding contact points positioned for seating below the equator of the eye interior.

3. An intraocular lens in accordance with claim 2 in which at least one of said protruding contact points of each of said support portions is positioned near the end of the corresponding support portion.

4. An intraocular lens in accordance with claim 1 in which said stabilizing portion extends outwardly from said position-fixation means.

5. An intraocular lens in accordance with claim 4 in which said position-fixation means has a single stem portion joined to said lens body and in which said position-fixation means and said stabilizing portion extend from said single stem portion of said position-fixation means.

6. An intraocular lens in accordance with claim 1 in which the first groove portion of the eye interior is in the cul-de-sac formed between the anterior and posterior capsules and each support portion has at least two protruding contact points for seating each of the respective support portions in said groove portion of the eye.

7. An intraocular lens in accordance with claim 1 in which the second groove portion of the eye interior is in the cul-de-sac formed between the anterior and posterior capsules and in which said stabilizing portion extends beyond the iris of the eye toward said second groove portion.

8. An intraocular lens in accordance with claim 1 in which said position fixation support portions are deformable toward each other in response to the force applied thereto prior to seating of the lens in the eye.

9. An intraocular lens in accordance with claim 1 in which said position fixation support portions are resiliently deformable to a condition in which the most remote portions of said position fixation support portions are spaced apart a distance not exceeding the maximum lateral extension of the lens body.

10. An intraocular lens in accordance with claim 9 in which said position fixation support portions cross each other when they are in the latter condition.

* * * * *